(12) United States Patent
Higo et al.

(10) Patent No.: US 7,631,759 B2
(45) Date of Patent: Dec. 15, 2009

(54) PACKAGING BAG

(75) Inventors: Naruhito Higo, Tsukuba (JP); Tetsuro Tateishi, Tsukuba (JP); Takeshi Ito, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 536 days.

(21) Appl. No.: 10/580,014

(22) PCT Filed: Nov. 12, 2004

(86) PCT No.: PCT/JP2004/016852
§ 371 (c)(1),
(2), (4) Date: Jul. 11, 2006

(87) PCT Pub. No.: WO2005/048910
PCT Pub. Date: Jun. 2, 2005

(65) Prior Publication Data
US 2007/0144928 A1      Jun. 28, 2007

(30) Foreign Application Priority Data
Nov. 19, 2003    (JP) .............................. 2003-389797

(51) Int. Cl.
*A61B 17/06* (2006.01)
*A61F 13/02* (2006.01)
(52) U.S. Cl. .................. 206/438; 206/440; 604/307
(58) Field of Classification Search ................. 206/438, 206/440, 441, 484, 471; 604/307
See application file for complete search history.

(56) References Cited

U.S. PATENT DOCUMENTS

| 5,505,306 A | 4/1996 | Akemi et al. |
| 5,950,830 A | 9/1999 | Trigger et al. |

FOREIGN PATENT DOCUMENTS

| JP | 7-80040 A | 3/1995 |
| JP | 10-511330 A | 11/1998 |
| JP | 11-79989 A | 3/1999 |
| WO | WO 96/19394 A1 | 6/1996 |

*Primary Examiner*—Stephen Garbe
*Assistant Examiner*—Kaushikkumar Desai
(74) *Attorney, Agent, or Firm*—The Nath Law Group; Susanne M. Hopkins; Mihsuhn Koh

(57) ABSTRACT

A packaging bag 1 according to the present invention comprises a pair of packaging films 7x, 7y that are disposed facing one another, and are sealed together around a perimeter thereof so as to form a housing portion 9 housing a plaster. On one of the packaging films 7x is provided a protrusion 10 that protrudes toward the other packaging film 7y. When the plaster 2 is packaged, only the protrusion 10 of the packaging film 7x contacts a plaster body 5. The portion contacted by the protrusion 10 is a portion, on the inside of the plaster body 5, that excludes an outer periphery of the plaster body 5. Therefore, even if adhesive sticks out of the outer periphery of the plaster body 5, this adhesive does not contact the packaging film 7x. As a result, the plaster 2 can be easily removed from the packaging bag 1.

4 Claims, 3 Drawing Sheets

PACKAGING BAG

This Application is the National Phase of International Application No. PCT/JP2004/016852 filed Nov. 12, 2004, which designated the U.S. and was not published under PCT Article 21(2) in English, and this application claims, via the aforesaid International Application, the foreign priority benefit of and claims the priority from Japanese Application No. 2003-389797, filed Nov. 19, 2003, the complete disclosures of which are incorporated herein by reference.

TECHNICAL FIELD

The present invention relates to a bag for packaging a plaster which is used for percutaneously administering a drug.

BACKGROUND ART

A plaster generally comprises a plaster body having a support and an adhesive layer laminated on one surface of the support, and a release film detachably attached on the adhesive layer. Moreover, a percutaneously absorbable drug is contained in an adhesive forming the adhesive layer.

Among such plasters, there are ones in which the adhesive together with the drug overflows out from an outer periphery of the plaster body. If such a plaster is sealed in a conventionally common flat packaging bag, then a problem arises in that the adhesive becomes attached to the inner surface of the packaging bag, and hence the plaster adheres to the packaging bag.

As a packaging bag for resolving this problem, one has been proposed in which a large number of small projections are formed over the whole of the inner surface of the packaging bag so as to reduce the contact area with the plaster (e.g. Japanese Patent No. 2814185).

However, even with a packaging bag such as that described in Japanese Patent No. 2814185, adhesive sticking out of the outer periphery of the plaster body cannot be prevented from contacting the projections, and hence the adhesion still occurs, and thus removing the plaster from the packaging bag is difficult.

DISCLOSURE OF THE INVENTION

Accordingly, it is an object of the present invention to provide a packaging bag from which the plaster can be easily removed.

To achieve the above object, the present invention provides a packaging bag for a plaster comprising a plaster body having a support and an adhesive layer laminated on one surface of the support, and a release film detachably attached to the adhesive layer, the packaging bag is characterized by comprising a pair of packaging films disposed facing one another and sealed together around a perimeter thereof so as to form a housing portion for the plaster, wherein a protrusion that projects out into the housing portion is provided on one of the packaging films, and when the plaster is packaged, the protrusion contacts the plaster body only at a portion of the plaster body excluding an outer periphery of the plaster body.

In this arrangement, one of the pair of packaging films in the packaging bag has thereon a protrusion that projects out into the packaging bag, i.e. toward the other packaging film, and hence the packaging films are separated from one another except at the protrusion. Moreover, the protrusion contacts only the plaster body, while it does not contact the outer periphery of the plaster body. Therefore, even if an adhesive constructing the adhesive layer sticks out from the outer periphery of the plaster body, this adhesive can be prevented or suppressed from contacting the packaging bag. Furthermore, the outer periphery of the plaster body and the vicinity thereof are not contacted or pressed by the protrusion, and hence pressing the adhesive out of the outer periphery of the plaster body is also prevented or suppressed.

Moreover, in the case that the protrusion is high, the gap between the packaging films other than at the protrusion is also increased. Therefore, in the case that an outer peripheral portion of the release film of the plaster extends outward beyond the outer periphery of the plaster body, by making the protrusion have at least a predetermined height, an outer peripheral portion of the packaging film on which the protrusion is formed can be separated away from the outer periphery of the plaster body. As a result, contact between adhesive sticking out of the outer periphery of the plaster body and the packaging bag can be prevented or suppressed more reliably.

It is preferable for the height of the protrusion to satisfy the relationships represented by following expressions (1) and (2).

$$(E+F)/A > F/C \quad (1)$$

$$(E+F)/a > F/c \quad (2)$$

Wherein, in expressions (1) and (2), "E" is the height (mm) of the protrusion, and "F" is the thickness (mm) of the plaster body. In expression (1), "A" is the length (mm) from an outer periphery of the housing portion to the outer periphery of the protrusion in a transverse direction which is one direction of the outer periphery of the plaster body, and "C" is the length (mm) from the outer periphery of the plaster body to an outer periphery of the release film in the transverse direction. In expression (2), "a" is the length (mm) from the outer periphery of the housing portion to the outer periphery of the protrusion in a longitudinal direction which is the other direction of the outer periphery of the plaster body, and "c" is the length (mm) from the outer periphery of the plaster body to the outer periphery of the release film in the longitudinal direction. By the protrusion having such a height, the outer peripheral portion of the packaging film on which the protrusion is formed can be separated away from the outer periphery of the plaster body more reliably.

To maintain the state of separation between the packaging films, the packaging films preferably have a suitable degree of strength/rigidity, and hence it is preferable for each of the packaging films to be a laminated film having an aluminum layer therein. Such a laminated film having an aluminum layer therein also has excellent air-tightness, and hence is suitable for packaging a drug-containing plaster.

EFFECTS OF THE INVENTION

With the structure of the present invention, even if a plaster for which adhesive tends to stick out is packaged, the adhesive will not become attached to the inner surface of the packaging bag, and hence adhering together of the plaster and the packaging bag can be prevented or suppressed, therefore removal of the plaster from the packaging bag can be facilitated.

BEST MODE FOR CARRYING OUT THE INVENTION

Figure 1:
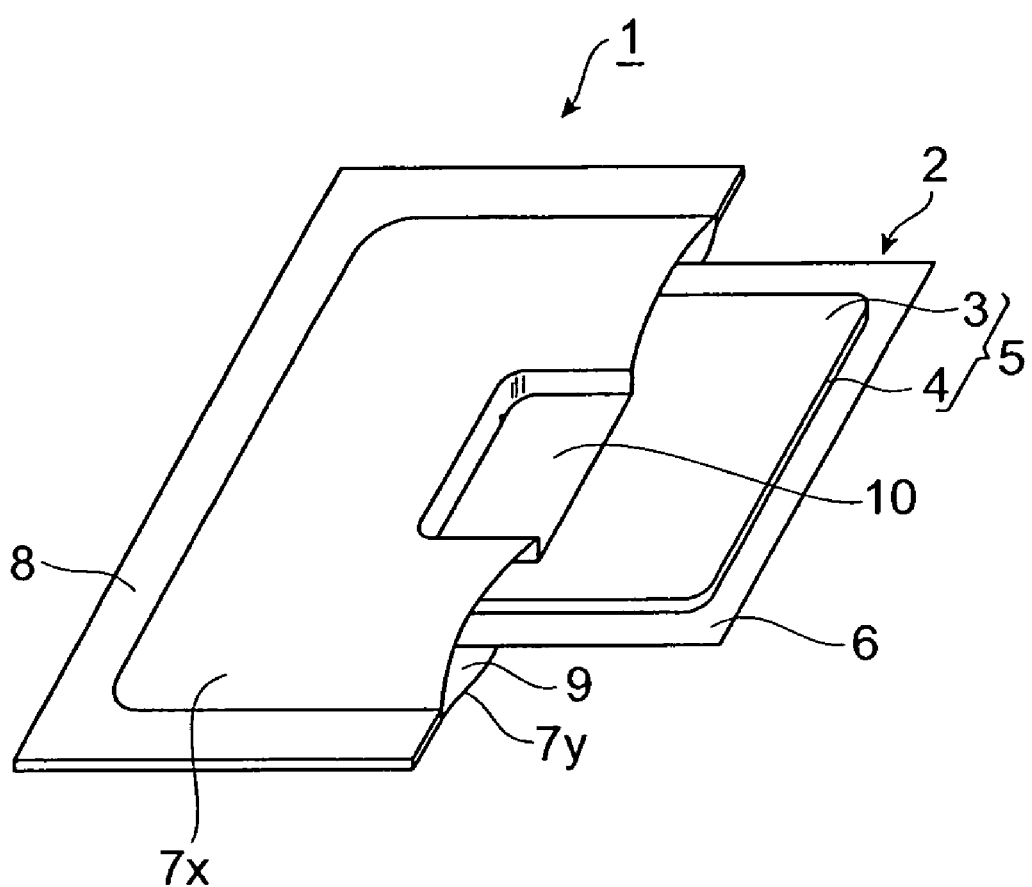
FIG. 1 is a partially cut away perspective view showing a packaging bag of the present invention with a plaster packaged therein.

Now, a preferred embodiment of the present invention will be described by referring to the drawings. Note that in the drawings, like references characters designate like or corresponding parts.

FIG. 1 is a partially cut away perspective view showing an embodiment of a packaging bag according to the present invention. The plaster 2 packaged by the packaging bag 1 according to the present embodiment comprises a plaster body 5 having a support 3 and an adhesive layer 4 laminated over substantially the whole of one surface of the support 3, and a release film 6 that is detachably attached to the adhesive layer 4. The plaster body 5 and the release film 6 each have a substantially rectangular shape in the illustrated embodiment, more specifically a substantially square shape (see FIG. 2). The release film 6 has a larger area than the plaster body 5, and has the plaster body 5 detachably attached to substantially the center thereof. This is for reasons such as to prevent spreading out of the adhesive of the adhesive layer 4 toward at least one side (the bottom in FIG. 1) in the case that the adhesive sticks out, or to facilitate peeling off of the release film 6.

There are no particular limitations on the constituent material of the support 3 so long as this is a material able to support the adhesive layer 4; a strechable or non-strechable material can be used. Specific examples of the material include a cloth or nonwoven cloth, or a sheet material made of a synthetic resin such as a polyurethane.

The adhesive that is the main material of the adhesive layer 4 may be an adhesive water-containing paste capable of fixing a drug to the skin surface for a long time at normal temperature, having added thereto water, thickeners, wetting agents, fillers, and in addition cross-linking agents, polymerization agents, solubilization agents, absorption promoters, drug effect adjuvants, stabilization agents, antioxidant agents, emulsifiers, drugs, and so on as required. Moreover, an acrylic adhesive, a rubber adhesive, a silicone adhesive, or the like is also preferable; of these a rubber adhesive is preferable from the viewpoint of adhesive properties and drug releasing ability. A drug is contained in or mixed into the adhesive; as the drug, any of various percutaneously absorbable drugs such as a general anesthetic, a sleeping drug, or an analgesic can be used. In the present embodiment, the drug-containing adhesive is assumed to have a characteristic of being prone to stick out of the outer periphery of the plaster body 5.

As the main material of the release film 6, a film of a resin such as polyethylene terephthalate, paper or the like that has been subjected to release treatment is selected as appropriate. The release film 6 preferably has a suitable degree of rigidity so that wrinkling or twisting of the plaster body 5 will not occur.

The packaging bag 1 according to the present embodiment for packaging the plaster 2 described above therein comprises a pair of substantially rectangular (more specifically substantially square) packaging films 7x, 7y disposed facing one another. Although not shown in the drawings, each of the packaging films 7x, 7y according to the present embodiment is a laminated film in which are laminated together a polyethylene terephthalate layer (PET layer), an aluminum layer, a PET layer, and a glycol-modified polyethylene terephthalate (polyethylene terephthalate glycol: PET-G) sealant layer in this order. The reason for providing the aluminum layer as an intermediate layer is because such an aluminum layer has excellent air-tightness, and has a suitable degree of strength/rigidity as described above. Moreover, the PET resin has low oxygen permeability, and the PET-G resin is heat-sealable and is strong against bending and twisting, and hence these are suitable as constituent materials of the packaging films 7x, 7y.

Figure 2:
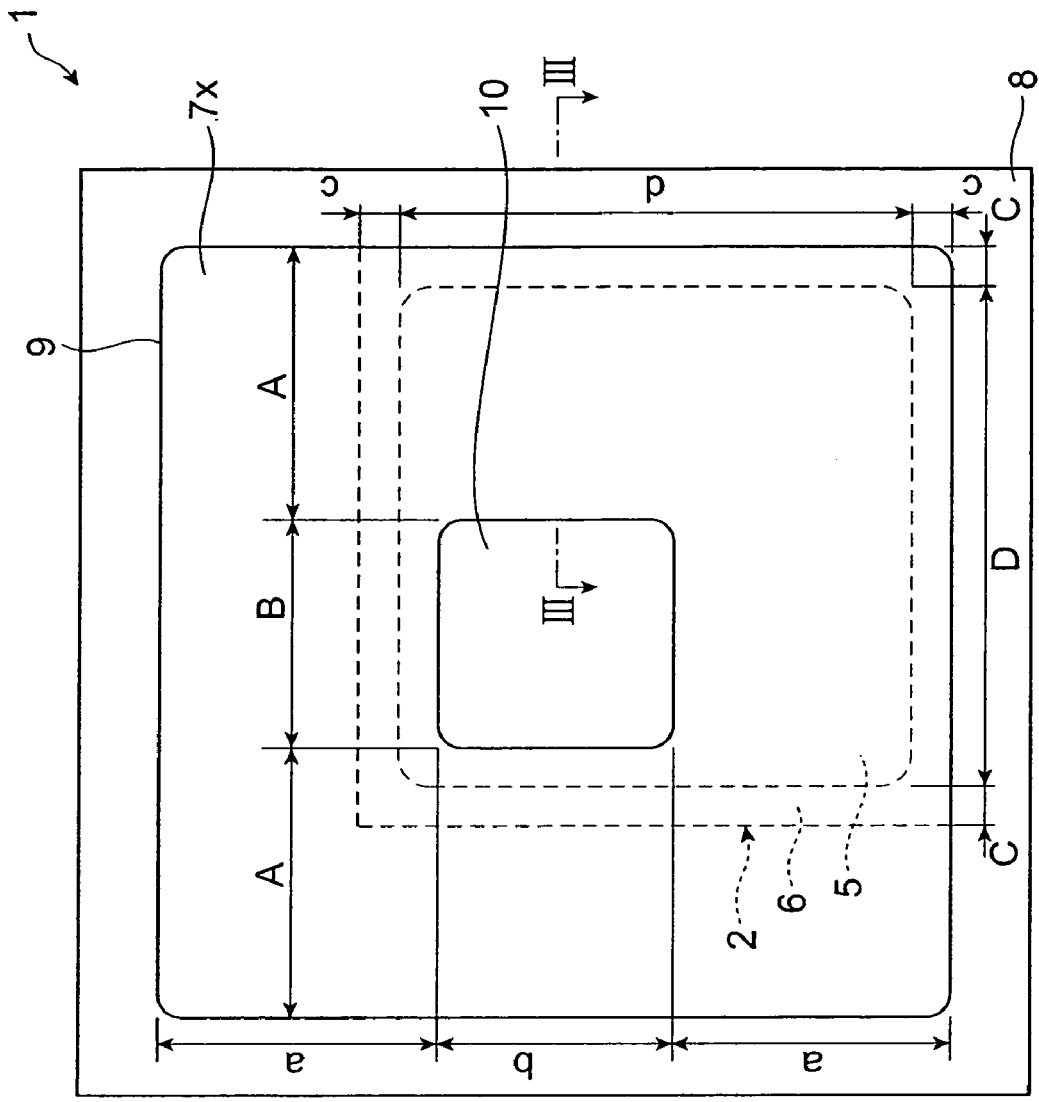
FIG. 2 is a front view of the packaging bag shown in FIG. 1.
Figure 3:
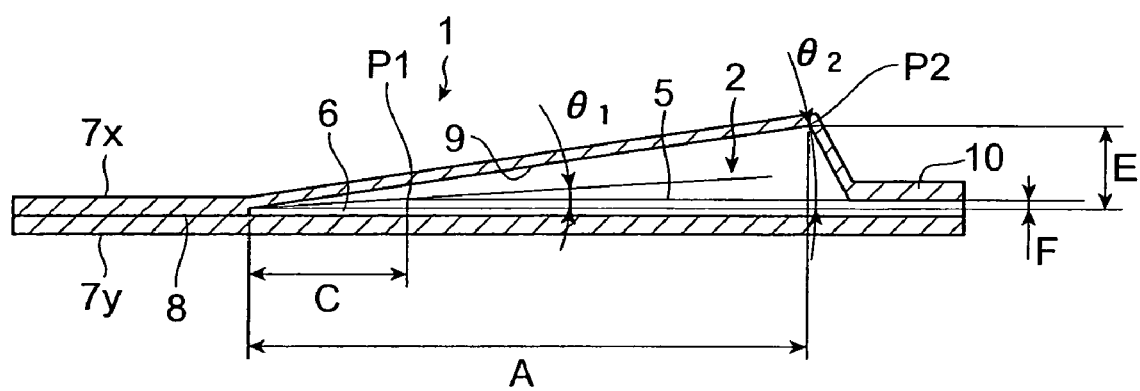
FIG. 3 is a cross-sectional view taken along the line III-III in FIG. 2, shown with dimensions exaggerated.

The pair of packaging films 7x, 7y disposed facing one another are sealed together around the whole of the perimeter as shown in FIGS. 2 and 3. In the present embodiment, the packaging films 7x, 7y are placed on one another such that the PET-G sealant layer of each is on the inside, and then the outer peripheral portions of the packaging films 7x, 7y are joined together by heat sealing. It should be noted that the sealing of the perimeter of the packaging films 7x, 7y may also be carried out using, for example, an adhesive instead of the heat sealing. In this way, a sealed portion 8 which is the outer peripheral portion for joining the packaging films 7x, 7y each other, and a housing portion 9 comprising a sealed region surrounded by the sealed portion 8 are formed in the packaging bag 1. The plaster 2 is housed in the housing portion 9 in a state with the plaster body 5 facing the packaging film 7x.

The packaging film 7x is provided with a protrusion or 10. The protrusion 10 protrudes into the packaging bag, i.e. in a direction toward the other packaging film 7y. The protrusion 10 is preferably formed by press molding or the like. Moreover, the protrusion 10 has a predetermined shape and dimensions; and in the embodiment shown in the drawings, a top surface of the protrusion 10 is a substantially rectangular (specifically substantially square) flat surface.

Referring to FIG. 2, which is a front view of the packaging bag 1 showing the packaging bag 1 together with the plaster 2 packaged therein, the plaster 2 is positioned in the bottom right corner of the housing portion 9 of the packaging bag 1, and in this position, the protrusion 10 is in contact with an inside portion of the plaster body 5. The inside portion means a portion inside of the outer periphery or outer edge of the plaster body 5. That is, the inside portion does not include the outer periphery of the plaster body 5. Moreover, it should be easy for persons skilled to appreciate that with the construction shown in FIG. 2, regardless of the position of the plaster 2 in the packaging bag 1, the above relationship, i.e. the relationship whereby the protrusion 10 contacts the inside portion of the plaster body 5 is satisfied. This relationship can be represented by following expressions (3) and (4).

$$A+B<C+D, \text{ and } 2A+B=2C+D+\alpha \quad (3)$$

$$a+b<c+d, \text{ and } 2a+b=2c+d+\beta \quad (4)$$

The expression (3) and (4) are based on FIG. 2. "A" is the length in a transverse direction, "a" is the length in a longitudinal direction from the sealed portion 8 to the protrusion 10, "B" is the length in the transverse direction, "b" is the length in the longitudinal direction of the protrusion 10, "C" is the length in the transverse direction, "c" is the length in the longitudinal direction from the outer periphery of the plaster body 5 to the outer periphery of the release film 6, "D" is the length in the transverse direction and "d" is the length in the longitudinal direction of the plaster body 5. Moreover, α and β in the expressions are for lengths of required manufacturing margins.

In the case that the relationships of expression (3) and (4) are satisfied, as described above, the protrusion 10 contacts only the inside portion of the plaster body 5, and does not cross the outer periphery of the plaster body 5. Moreover, due to the presence of the protrusion 10, the packaging film 7x and the packaging film 7y contact one another only at the protrusion 10, being separated from one another at the outer peripheral portion which is the portion excluding the protrusion 10 (see FIG. 3). Therefore, there is low possibility that the outer periphery of the plaster body 5 facing the packaging film 7x side contacts with the packaging film 7x. Even if the drug-containing adhesive leaks out from the outer periphery of the plaster body 5, adhering together of the packaging film 7x and the plaster 2 can be greatly suppressed.

Now, even if the above relationships are satisfied, depending on the height of the protrusion 10, the gap between the packaging films 7x, 7y around the protrusion 10 will be narrow, and hence one can envisage that the outer periphery of the plaster body 5 might contact the packaging film 7x. Based on FIG. 3, which is an enlarged sectional view taken along the line III-III in FIG. 2, we will now examine the conditions under which the outer periphery of the plaster body 5 does not contact the packaging film 7x.

First, the state in which there is the highest possibility of the outer periphery of the plaster body 5 contacting the packaging film 7x is thought to be when the outer periphery of the plaster 2 is in contact with the outer periphery of the housing portion 9 of the packaging bag 1. FIG. 3 shows this state drawn exaggeratedly.

Here, relative to the inner surface of the packaging film 7y (the upper surface in FIG. 3), take the angle of the line joining the outer periphery of the housing portion 9 with the outer periphery P1 of the plaster body 5 to be angle $\theta_1$, and take the angle of the line joining the outer periphery of the housing portion 9 with the outer periphery P2 of the protrusion 10 to be angle $\theta_2$. In the case that angle $\theta_2$ is greater than angle $\theta_1$, so long as the packaging film 7x does not bend, then as can be seen from FIG. 3, it will be theoretically impossible for the outer periphery of the plaster body 5 to contact the packaging film 7x.

As described above, the condition under which the outer periphery of the plaster body 5 does not contact the packaging film 7x is:

$\theta_2 > \theta_1$, and, $$\tan\theta_2 > \tan\theta_1 \qquad (5)$$

For expression (5), because angle $\theta_1$ and angle $\theta_2$ are very small in practice, as shown in FIG. 3, taking the height of the protrusion 10 to be "E" and taking the thickness of the plaster body 5 to be "F", expression (5) can be approximated by following expression (6).

$$(E+F)/A > F/C \qquad (6)$$

The above description relates to the transverse direction in FIG. 2, i.e. the direction of line III-III, but similar applies for the longitudinal direction in FIG. 2, with the outer periphery of the plaster body 5 not contacting the packaging film 7x in theory in the case that following expression (7) is satisfied.

$$(E+F)/a > F/c \qquad (7)$$

It should be noted that because the packaging films 7x, 7y and the plaster 2 are bendable, there is a possibility that the outer periphery of the plaster body 5 may contact the packaging film 7x even if expressions (3) to (7) are satisfied; nevertheless, as described above, a release film 6 having relatively high rigidity is used, and moreover the packaging films 7x, 7y also have some degree of rigidity due to the use of an aluminum laminated film, and hence contact of the outer periphery of the plaster body 5 with the packaging film 7x can be greatly reduced.

The above-mentioned expressions will now be further described using specific numerical values. For example, assume that the lengths "A" to "D" and "F", and the lengths "a" to "d" satisfy the following relationships.

$2A+B=2a+b=62$ (mm)

$C=c=2.5$ (mm)

$D=d=40.3$ (mm)

$F=0.3$ (mm)

According to these numerical values and expressions (3) and (4), the relationship between the length "A" in the transverse direction from the outer periphery of the protrusion 10 to the outer periphery of the housing portion 9 and the length "B" in the transverse direction of the protrusion 10 is in accordance with the following expression (8), and the relationship between the length "a" in the longitudinal direction from the outer periphery of the protrusion 10 to the outer periphery of the housing portion 9 and the length "b" in the longitudinal direction of the protrusion 10 is in accordance with the following expression (9).

$$A>19.2, \text{ and } B<23.6 \qquad (8)$$

$$a>19.2, \text{ and } b<23.6 \qquad (9)$$

Moreover, by the above numerical values and expression (6) and (7), the height "E" of the protrusion 10 can be represented by following expression (10) using the length "A" in the transverse direction and the length "a" in the longitudinal direction from the outer periphery of the protrusion 10 to the outer periphery of the housing portion 9.

$$E>0.12\times A-0.3, \text{ and } E>0.12\times a-0.3 \qquad (10)$$

Therefore, according to this example, for the plaster body 5 and the packaging film 7x of the packaging bag 1 to contact one another at only the protrusion 10, with there being no contact at the outer periphery of the plaster body 5, in each of the longitudinal direction and the transverse direction, the distance from the outer periphery of the protrusion 10 to the outer periphery of the housing portion 9 should be longer than 19.2 mm, and the width of the upper end surface of the protrusion 10 should be less than 23.6 mm. Furthermore, in the case that the length from the outer periphery of the protrusion 10 to the outer periphery of the housing portion 9 is 19.2 mm in each of the transverse direction and the longitudinal direction, the height of the protrusion 10 should be at least approximately 2.0 mm.

It should be possible to understand the operation and effects of the packaging bag 1 according to the present embodiment from the above, but these will be described simply below.

In the case that a plaster 2 that has the construction described above and satisfies expressions (3) and (4) is housed and sealed in a packaging bag 1 that has the construction described above and satisfies expressions (3) and (4), regardless of the position of the plaster 2 relative to the packaging bag 1, out of the packaging bag 1 only the protrusion 10 will contact the plaster body 5, and furthermore the protrusion 10 will not contact the outer periphery of the plaster body 5. Therefore, even if the adhesive of the adhesive layer 4 sticks out of the outer periphery of the plaster body 5, adhering together of the packaging film 7x and the plaster 2 due to the adhesive can be suppressed. The adhesive sticking out is prevented from flowing toward the other packaging film 7y by the release film 6 which is larger than the plaster body 5, and hence adhering together of the plaster 2 and the packaging film 7y will obviously not occur. As the result, removing the plaster 2 from the packaging bag 1 is easy.

In addition, in the case that expressions (5) to (7) are satisfied, then regardless of the position of the plaster 2, there will be substantially no contact of the outer periphery of the plaster body 5 with the packaging film 7x, and hence the effect of preventing adhering together, and the effect of facilitating removal of the plaster can be further improved.

Furthermore, there is also an effect of the protrusion 10 pushing against the plaster 2, and hence an effect of movement of the plaster 2 within the housing portion 9 being suppressed can also be expected. That is, the plaster 2 moving toward the outside of the packaging bag 1 is suppressed, and hence contact between the outer periphery of the plaster body 5 and the packaging film 7x is also prevented or suppressed.

Although a preferred embodiment of the present invention has been described in detail above, the present invention should not be limited by any of the above described exemplary embodiment.

For example, in the above embodiment, the shape of the packaging bag 1 and the shape of the top surface of the protrusion 10 are substantially square, but this shape depends on the shape of the plaster to be housed in the packaging bag 1, and may be a rectangle comprising long sides and short sides, or another shape such as a circle.

Moreover, the top surface of the protrusion 10 was made to be flat, but other than this, for example this top surface may be a corrugated surface, or a surface having a large number of small projections provided thereon and closely spaced each other. It should be noted that even in the case of a surface having the small projections, the region demarcated by the projections positioned outermost must be positioned within the inside portion of the plaster body from which the outer periphery of the plaster body is excluded as described above. Furthermore, the top surface of the protrusion 10 may also be a curved surface of a hemispherical shape or the like.

Moreover, in the embodiment described above, the protrusion 10 is press-molded, but other than this, the protrusion 10 may be formed by bonding a cushioning material to the center of the inner surface of the packaging film 7x.

INDUSTRIAL APPLICABILITY

As described above, according to the packaging bag of the present invention, even if a plaster for which adhesive tends to stick out is packaged, the adhesive will not become attached to the inner surface of the packaging bag, and hence adhering between the plaster and the packaging bag can be prevented or suppressed, whereby removal of the plaster from the packaging bag can be facilitated. There is thus much scope for use of the present invention in the pharmaceutical industry where plasters are used.

The invention claimed is:

1. A packaging bag for a plaster, the plaster including a plaster body, a support and an adhesive layer laminated on one surface of the support and having a plaster outer periphery, and a release film having a release outer periphery and being detachably attached to the adhesive layer, the packaging bag, comprising:
a pair of packaging films comprising first packaging film having a first perimeter and an opposing second packaging film having a second perimeter, the first packaging film and the second packaging film being sealed together at the first and second perimeters thereby forming an interior housing portion having a housing outer periphery for housing the plaster,
the first packaging film or the second packaging film comprising a protrusion having a protrusion outer periphery and protruding into the interior housing portion and configured such that when the plaster is packaged in the packaging bag, the protrusion contacts a portion of the plaster body excluding the plaster outer periphery, the protrusion having a height such that when the release outer periphery extends outward beyond the plaster outer periphery, an outer peripheral portion of the packaging film on which the protrusion is formed is separated away from the plaster outer periphery,
wherein an angle θ2 formed by a line joining the housing outer periphery with the protrusion outer periphery is greater than an angle θ1 formed by a line joining the housing outer periphery with the plaster outer periphery, so that the plaster outer periphery does not contact the packaging film on which the protrusion is formed.

2. The packaging bag according to claim 1, wherein the packaging bag satisfies the relationships represented by the following expression:

$$(E+F)/A > F/C \qquad (1)$$

$$(E+F)/a > F/c \qquad (2)$$

wherein, "E" is the height (mm) of the protrusion,
"F" is the thickness (mm) of plaster body,
"A" is the length (mm) from the housing outer periphery to the protrusion outer periphery in a transverse direction which is one direction of the plaster outer periphery
"C" is the length (mm) from the plaster outer periphery to the release outer periphery in the transverse direction,
"a" is the length (mm) from the housing outer periphery to the protrusion outer periphery in a longitudinal direction which is the other direction of the plaster outer periphery, and
"c" is the length (mm) from the plaster outer periphery to the release outer periphery in the longitudinal direction.

3. The packaging bag according to claim 1, wherein each of the first and the second packaging films is a laminated film comprising an aluminum layer.

4. The packaging bag according to claim 2, wherein each of the first and the second packaging films is a laminated film comprising an aluminum layer.

* * * * *

UNITED STATES PATENT AND TRADEMARK OFFICE
CERTIFICATE OF CORRECTION

PATENT NO. : 7,631,759 B2 Page 1 of 1
APPLICATION NO. : 10/580014
DATED : December 15, 2009
INVENTOR(S) : Naruhito Higo et al.

It is certified that error appears in the above-identified patent and that said Letters Patent is hereby corrected as shown below:

Column 8, Claim 2, Line 31
Please delete "expression"
and replace with -- expressions --

Signed and Sealed this

Sixteenth Day of February, 2010

David J. Kappos
*Director of the United States Patent and Trademark Office*